United States Patent [19]

Teall

[11] Patent Number: 5,627,211
[45] Date of Patent: May 6, 1997

[54] CYCLOHEXYL AMINE DERIVATIVES AND THEIR USE AS TACHYKININ ANTAGONISTS

[75] Inventor: Martin R. Teall, Bishop Storford, United Kingdom

[73] Assignee: Merck Sharp & Dohme Limited, Hoddesdon, England

[21] Appl. No.: 397,234

[22] PCT Filed: Sep. 16, 1993

[86] PCT No.: PCT/GB93/01961

§ 371 Date: Mar. 13, 1995

§ 102(e) Date: Mar. 13, 1995

[87] PCT Pub. No.: WO94/07843

PCT Pub. Date: Apr. 14, 1994

[30] Foreign Application Priority Data

Sep. 25, 1992 [GB] United Kingdom .............. 9220286

[51] Int. Cl.⁶ .............. A61K 31/24; C07C 271/24; C07C 229/28; C07C 211/34
[52] U.S. Cl. .............. 514/539; 514/563; 514/647; 560/27; 562/444; 564/307
[58] Field of Search .............. 560/9, 12, 13, 560/17, 21, 22, 23, 27; 562/430, 435, 452, 444; 564/152, 153, 154, 157, 161, 162, 163, 164, 165, 166, 168, 171, 306, 307; 558/411, 412, 413; 514/539, 563, 647

[56] References Cited

FOREIGN PATENT DOCUMENTS 0436334  7/1991  European Pat. Off. .
0499313  8/1992  European Pat. Off. .

OTHER PUBLICATIONS

Takehisa, et al., Chem. Pharm. Bull. 24(8), pp. 1691–1697 1976.

*Primary Examiner*—Gary Geist
*Assistant Examiner*—Joseph M. Conrad
*Attorney, Agent, or Firm*—J. Eric Thies; David L. Rose

[57] ABSTRACT

Compounds of formula (I), and salts and prodrugs thereof wherein X, $R^2$, $R^3$, $R^4$, $R^5$, $R^7$ and $R^8$ are defined herein, are tachykinin receptor antagonists.

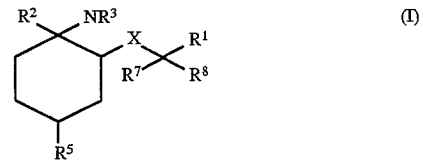

14 Claims, No Drawings

CYCLOHEXYL AMINE DERIVATIVES AND THEIR USE AS TACHYKININ ANTAGONISTS

This invention relates to a class of cyclic compounds, which are useful as tachykinin antagonists. More particularly, the compounds of the invention comprise a cyclohexyl ring system substituted by an arylmethyloxy or arylmethylthio moiety, phenyl and an optionally substituted amino group.

The tachykinins are a group of naturally-occurring peptides found widely distributed throughout mammalian tissues, both within the central nervous system and in the peripheral nervous and circulatory systems. The three known mammalian tachykinins are: substance P, neurokinin A and neurokinin B:

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitus, inflammatory diseases of the gut including ulcerative colitis and Crohn disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

We have now found a class of non-peptides which are potent antagonists of tachykinin.

European patent application no. 0 436 334 discloses 4- to 7-membered azacyclic compounds substituted at the 3-position by a benzyl substituted amino moiety and at the 2-position by an aryl moiety. The compounds are said to be tachykinin antagonists.

The present invention provides a compound of formula (I), or a salt or prodrug thereof:

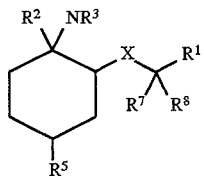

wherein

X represents O or S;

$R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$;

$R^2$ represents phenyl optionally substituted by $C_{1-6}$alkyl, $C_{1-6}$alkoxy, halo or trifluoromethyl;

$R^3$ and $R^4$ each independently represent H, $COR^a$, $CO_2R^a$ or $C_{1-6}$alkyl optionally substituted by a group selected from ($CO_2R^a$, $CONR^aR^b$, hydroxy, cyano, $COR^a$, $NR^aR^b$, and phenyl optionally substituted by $C_{1-6}$alkyl, $C_{1-6}$alkoxy, halo or trifluoromethyl);

$R^5$ represents H or $XCH_2R^6$ wherein $R^6$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$ and X is as previously defined;

$R^7$ and $R^8$ each independently represent H or $C_{1-6}$alkyl; and $R^a$ and $R^b$ each independently represent H, $C_{1-6}$alkyl, phenyl or trifluoromethyl.

As used herein, the definition of each expression, when it occurs more than once in any structure, is intended to be independent of its definition elsewhere in the same structure.

The alkyl, alkenyl and alkynyl groups referred to with respect to the above formula may represent straight, branched or cyclic groups or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

A subgroup of compounds according to the invention is represented by compounds of formula (I) wherein $R^7$ and $R^8$ each represent H, and salts and prodrugs thereof.

Preferably X represents O.

Preferably $R^1$ represents substituted phenyl. When $R^1$ is substituted phenyl suitable substituents include $C_{1-6}$alkyl, nitro, trifluoromethyl, trimethylsilyl, bromo, chloro, fluoro, iodo, cyano, methyl, ethyl, cyclopropyl, vinyl, methoxy, phenoxy, amino and carbonylmethoxy. Preferably $R^1$ represents phenyl substituted by one or more groups selected from methyl and trifluoromethyl. More preferably $R^1$ represents disubstituted phenyl, especially 3,5-dimethylphenyl or 3,5-bis(trifluoromethyl)phenyl.

Preferably $R^2$ represents unsubstituted phenyl.

Suitable values for $R^3$ and $R^4$ include H, $C_{1-6}$alkyl, such as methyl, and substituted $C_{1-6}$alkyl, such as $C_{1-6}$alkyl, preferably $CH_{1-4}$alkyl, more preferably $CH_2$, substituted by $CONR^{10}R^{11}$, especially $CONH_2$, or $CO_2R^a$, such as $CO_2CH_3$.

Preferably at least one of $R^3$ and $R^4$ represents H. More preferably one of $R^3$ and $R^4$ represents H and the other of $R^3$ and $R^4$ represents H or $CH_2CONH_2$.

Preferably $R^5$ represents H.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, oxalic acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

A particular sub-class of compounds according to the invention is represented by compounds of formula (Ia), and salts and prodrugs thereof:

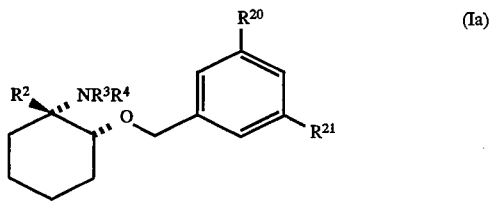

(Ia)

wherein $R^2$, $R^3$ and $R^4$ are as defined for formula (I); and $R^{20}$ and $R^{21}$ independently represent H $C_{1-6}$alkyl, $C_{2-6}$alkenyl, $C_{2-6}$alkynyl, halo, cyano, nitro, trifluoromethyl, trimethylsilyl, $OR^a$, $SR^a$ $SOR^a$, $SO_2R^a$, $NR^aR^b$, $NR^aCOR^b$, $NR^aCO_2R^b$, $COR^a$ or $CONR^aR^b$, where $R^a$ and $R^b$ are as previously defined.

Preferably $R^{20}$ and $R^{21}$ are selected from H, $C_{1-6}$alkyl, such as t-butyl, ethyl or methyl, $C_{1-6}$alkoxy, such as methoxy, halo, such as chloro, bromo or iodo, and trifluoromethyl.

The substance P antagonizing activity of the compounds described herein was evaluated using the human NK1R assay described in published European patent application no. 0 528 495. The method essentially involves determining the concentration of the test compound required to reduce by 50% the amount of radiolabelled substance P binding to human NK1R, thereby affording an $IC_{50}$ value for the test compound. The compounds of Examples 1, 5 and 6 were found to have $IC_{50}$ values of 100 nM, 350 nM and 100 nM, respectively.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) are of value in the treatment of a wide variety of clinical conditions which are characterized by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotropic lateral sclerosis (ALS; Lou Gehrig's disease) and other neuropathological disorders such as peripheral neuropathy, for example, diabetic or chemotherapy-induced neuropathy, and postherpetic and other neuralgias; small cell carcinoma such as small cell lung cancer; respiratory diseases such as chronic obstructive airways disease, bronchopneumonia, bronchospasm and asthma; inflammatory diseases such as inflammatory bowel disease, irritable bowel syndrome, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like, and proliferative vitreoretinopathy; cutaneous diseases such as contact dermatitis, atropic dermatitis, urticaria, and other eczematoid dermatitis; oedema, such as oedema caused by thermal injury; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as cystitis and bladder detrusor hyperreflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

The compounds according to the invention wherein $R^3$ and $R^4$ both represent H may be prepared by a process which comprises treatment of an intermediate of formula (II):

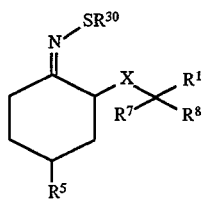
(II)

wherein $R^1$, $R^5$, $R^7$, $R^8$ and X are as defined for formula (I) and $R^{30}$ represents an alkyl or, preferably, a phenyl group, with a reagent of formula $R^2$—M, where $R^2$ is as defined for formula (I) and M represents an alkali metal, such as lithium.

The reaction is conveniently effected in a suitable organic solvent, such as an ether, for example, tetrahydrofuran.

Compounds of formula (I) where one or both of $R^3$ and $R^4$ and are other than H may be prepared from compounds of formula (I) wherein both of $R^3$ and $R^4$ represent H by conventional procedures, for example, reaction with a suitable alkylating or acylating agent. Suitable procedures are described in the accompanying examples, and further procedures will be readily apparent to those skilled in the art.

Intermediates of formula (II) may be prepared from compounds of formula (III):

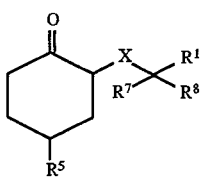
(III)

wherein $R^1$, $R^5$, $R^7$, $R^8$ and X are as defined for formula (I), by reaction with a compound of formula $R^{30}$—S—S—$R^{30}$ in the presence of ammonia and a nitrite, such as, for example, silver nitrite.

Compounds of formula (III) may be prepared by oxidation of the corresponding alcohols of formula (IV):

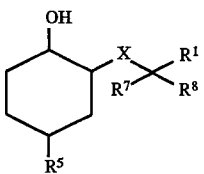
(IV)

wherein $R^1$, $R^5$, $R^7$, $R^8$ and X are as previously defined by conventional methods.

Conveniently the oxidation is effected under Swern conditions, i.e. with the use of oxalyl chloride in the presence of dimethyl sulphoxide. Other suitable oxidation procedures will be readily apparent to those skilled in the art.

Compounds of formula (IV) may be prepared by reaction of compounds of formula (V) with compounds of formula (VI):

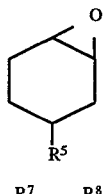
(V)

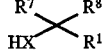
(VI)

wherein $R^1$, $R^5$, $R^7$, $R^8$ and X are as previously defined, in the presence of a base.

Suitable bases of use in reaction include metal hydrides, such as, for example, potassium hydride, and alumina.

The compound of formula (V) wherein $R^5$ is H is commercially available.

The compounds of formula (V) wherein $R^5$ is $XCH_2R^6$ may be prepared by reaction of a compound of formula (VII) with a compound of formula (VIII):

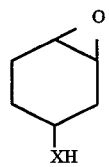
(VII)

(VIII)

wherein X and $R^1$ are as previously defined and L represents a leaving group such as halo, for example, bromo or iodo.

Compounds of formulae (VII) and (VIII) are commerically available or may be prepared from commercially available starting materials by known procedures.

Where the above-described process for the preparation of the compounds according to the invention gives rise to mixtures of stereoisomers these isomers may, if desired, be separated, suitably by conventional techniques such as preparative chromatography.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

1-(3,5-Dimethylbenzyloxy)-2-amino-2-phenylcyclohexane a) A toluene (70 ml) solution containing cyclohexene oxide (20 g), 3,5-dimethylbenzyl alcohol and alumina (5 g) was heated at reflux for 16 h with azeotrophic removal of water. The solution was filtered and the solvent removed in vacuo to give 1-(3,5-dimethylbenzyoxy)-2-hydroxycyclohexyl as an oil.

b) The product of Example 1a (10 g) was oxidized under standard Swern conditions (JOC, 1978, 43, 2480) using oxalyl chloride (4.12 ml) and dimethyl sulphoxide (6.7 ml). The product was purified on silica gel eluting with petroleum ether-ethyl acetate mixtures to give 1-(3,5-dimethylbenzyoxy)-2-cyclohexanone as an oil. $^1$H NMR (360 MHz, $CDCl_3$) ? δ 1.61–1.96 (6H, m), 2.16–2.27 (1H, m), 2.30 (6H, s), 2.52–2.57 (1H, m), 3.85–3.90 (1H, m), 4.39, 4.68 (2H, ABq, J=11.6 Hz), 6.97 (2H, s) and 6.92 (1H, s).

c) The product of Example 1b (6.90 g) was converted into the corresponding sulphenimine using the procedure of Davis (JOC, 1973, 38, 2809) by treatment with silver nitrate (4.9 g), phenyl disulphide (6.5 g) and ammonia. The crude product was purified on silica gel eluting with petroleum ether-ethyl acetate mixtures to give 1-(3,5-dimethylbenzyoxy)-2-phenyl sulphenimine cyclohexane.

$^1$H NMR (360 MHz, CDCl$_3$) δ 1.42–1.62 (2H, m), 1.68–1.76 (1H, m), 1.86–1.93 (2H, m), 2.07–2.12 (1H, m), 2.30 (6H, s), 2.44–2.64 (2H, m), 4.03 (1H, t, J=3.6 Hz), 4.36–4.50 (2H, ABq, J=11.7 Hz), 6.91 (1H, s), 6.96 (2H, s) and 7.16–7.57 (5H, m).

d) 1-(3,5-Dimethylbenzyoxy)-2-phenylsulphenimine cyclohexane (Example 1c, 5.80 g) was dissolved in ether (100 ml) at 0° C. Phenyllithium (17.1 ml) was added and after 1 hour the reaction mixture was heated to reflux. The reaction was quenched with 2M-sodium hydroxide (100 ml) and the product extracted into ethyl acetate (3×50 ml). The combined organic phase was washed with water (2×50 ml), saturated sodium chloride (50 ml), dried (MgSO$_4$) and evaporated in vacuo. The product was purified on silica eluting with petroleum ether-ethyl acetate mixtures to give 1-(3,5-dimethylbenzyoxy)-2-amino-2-phenylcyclohexane as a crystalline solid. mp=75°–78° C. $^1$H NMR (360 MHz, CDCl$_3$) δ 1.18–1.23 (2H, m), 1.25–1.31 (1H, m), 1.42–1.48 (2H, m), 1.88–1.92 (1H, m), 2.03–2.10 (1H, m), 2.24 (6H, s), 2.34–2.38 (1H, m), 4.38 (1H, brs), 4.45, 4.51 (2H, ABq, J=11 Hz), 6.88 (2H, s), 6.90 (1H, s), 7.15–7.25 (3H, m) and 7.47–7.49 (2H, m). Found: C, 65.88; H, 7.67; N, 3.39; C$_{21}$H$_{27}$NO. C$_2$H$_2$O$_4$ (H$_2$O) requires C, 66.16; H, 7.48; N, 3.36%.

EXAMPLE 2

1-(3,5-Dimethylbenzyloxy)-2-dimethylamino-2-phenylcyclohexane

To a solution of acetic acid (1.6 ml) formaldehyde (1.10 ml) and sodium cyanoborohydride (0.7 g) was added 1-(3,5-dimethylbenzyoxy)-2-amino-2-phenylcyclohexane (1.7 g, Example 1d) in methanol. After stirring the solution for 2 hours, ethyl acetate and water was added and the organic phase dried (MgSO$_4$). Evaporation of the solvent in vacuo and column chromatography on silica gel (eluting with petroleum ether-ethyl acetate mixtures) gave the title compound. $^1$H NMR (360 MHz, CDCl$_3$) δ 1.18–1.25 (4H, m), 1.56–1.64 (2H, m), 1.99 (6H, s), 2.02–2.10 (1H, m), 2.32 (6H, s), 2.37–2.49 (1H, m), 4.10–4.13 (1H, m), 4.50, 4.69 (2H, ABq, J=11.8 Hz), 6.93 (1H, s), 7.07 (2H, s) and 7.17–7.33 (5H, m). Found: C, 80.56; H, 9.06; N, 4.39; C$_{23}$H$_{31}$NO. (0.25) H$_2$O requires C, 80.77; H, 9.28; N, 4.09%.

EXAMPLE 3

1-(3,5-Dimethylbenzyoxy)-2-methoxycarbonylmethylamino-2-phenylcyclohexane

A solution of 1-(3,5-dimethylbenzyoxy)-2-amino-2-phenylcyclohexane (0.6 g, Example 1d), methylbromoacetate (0.38 ml) and triethylamine (0.54 ml) in tetrahydrofuran (30 ml) was heated to reflux for 6 hours. After evaporation of the solvent the residue was redissolved in ethyl acetate (50 ml) which was washed with water (50 ml), saturated sodium chloride (50 ml), dried (MgSO$_4$) and evaporated in vacuo. The residue was purified by column chromatography on silica gel eluting with petroleum ether-ethyl acetate mixtures to give the title compound. $^1$H NMR (250 MHz, CDCl$_3$) δ 1.20–1.35 (2H, m), 1.58–1.84 (4H, m), 1.88–2.0 (2H, m), 2.24 (6H, s), 3.16, 3.24 (2H, ABq, J=15 Hz), 3.50 (1H, m), 3.71 (3H, s), 4.08, 4.31 (2H, ABq, J=12 Hz), 6.68 (2H, s), 6.84 (1H, s) and 7.22–7.48 (5H, m).

EXAMPLE 4

1-(3,5-Dimethylbenzyoxy)-2-(carboxamido) methylamino-2-phenylcyclohexane

Ammonia gas was bubbled through a cooled solution of 1-(3,5-dimethylbenzyoxy)-2-methoxycarbonylmethylamino-2-phenylcyclohexane (0.38 g, Example 3) in methanol (20 ml). After 16 hours the solvent was removed in vacuo and the residue purified by column chromatography on silica gel eluting with petroleum ether-ethyl acetate mixtures to give the title compound; m/e FAB 368 (M+H). $^1$H NMR (360 MHz, CDCl$_3$) δ 1.37–1.40 (2H, m), 1.58–1.94 (6H, m), 2.15 (6H, s), 2.78–2.83 (2H, m), 2.93–2.99 (1H, m), 3.40–3.42 (1H, m), 3.89, 4.22 (2H, ABq, J=11.8 Hz), 6.50 (2H, s), 6.79 (1H, s), 7.01 (1H, brs) and 7.21–7.42 (5H, m).

The oxalate salt was recrystallized from ethanol/water. mp 72°–76° C. Found: C, 63.80; H, 7.06; N, 5.54; C$_{23}$H$_{30}$N$_2$O$_2$.1.25(C$_2$H$_2$O$_4$) requires C, 63.93; H, 6.83; N, 5.84%.

EXAMPLE 5

1-(Bis-3,5-trifluoromethylbenzyoxy)-2-amino-2-phenylcyclohexane

The title compound was prepared using an analogous procedure as outlined in Example 1 but using Bis-3,5-trifluoromethylbenzyl alcohol. $^1$H NMR (360 MHz, DMSO) δ 1.40–1.52 (2H, m), 2.61–2.73 (2H, m), 2.78–2.84 (2H, m), 1.98–2.04 (1H, m), 2.06–2.09 (1H, m), 4.02 (1H, t, J=6.3 Hz), 4.50, 4.79 (2H, ABq, J=12.9 Hz), 7.33–7.43 (3H, m), 7.59–7.61 (2H, m), 7.85 (2H, s) and 7.96 (1H, s). The oxalate salt was recrystallized from ethanol/water mp 119°–122° C. Found: C, 53.96; H, 4.48; N, 2.70; C$_{21}$H$_{21}$F$_6$NO.C$_2$H$_2$O$_4$.(0.25)H$_2$O; C, 53.96; H, 4.62; N, 2.73%.

EXAMPLE 6

1-(Bis-3,5-trifluoromethylbenzyoxy)-2-(carboxamido)methylamino-2-phenylcyclohexane The title compound was prepared using an analogous procedure as outlined in Example 4. $^1$H NMR (360 MHz, DMSO) δ 1.30–1.44 (2H, m), 1.48–1.58 (1H, m), 1.59–1.64 (2H, m), 1.84–2.06 (2H, m), 2.08–2.16 (2H, m), 2.96, 3.12 (2H, ABq, J=15.6 Hz), 4.04–4.14 (1H, m), 4.43, 4.75 (2H, ABq, J=12.6 Hz), 7.30–7.56 (5H, m), 7.90 (2H, s) and 7.98 (1H, s). The oxalate salt was recrystallized in ethanol/water mp=48°–50° C. Found: C, 54.65; H, 5.19; N, 4.88 requires C$_{23}$H$_{22}$N$_2$O$_2$F$_6$.(0.6)C$_2$H$_2$O$_4$.(0.25)H$_2$O; C, 54.53; H, 4.86; N, 5.25%.

EXAMPLE 7

1,5-Bis-(3,5-dimethylbenzyloxy)-2-amino-2-phenylcyclohexane

The title compound was prepared using an analogous procedure as outlined in Example 1 using 4-(3,5-dimethylbenzyoxy)cyclohexene oxide. $^1$H NMR (360 MHz, DMSO) δ 1.44–1.68 (2H, m), 1.68–2.10 (4H, m), 2.19 (6H, s), 2.23 (6H, s), 2.40–2.51 (2H, m), 3.58–3.65 (1H, m), 3.68–3.75 (1H, m), 4.10–4.43 (4H, m) and 6.60–7.62 (11H, m). The oxalate salt was recrystallized in petroleum ether-ethyl acetate. mp=103°–105° C. Found: C, 69.66; H, 7.45; N, 2.53, requires C$_{30}$H$_{37}$NO$_2$.C$_2$H$_2$O$_4$.(0.25)H$_2$O; C, 69.36; H, 7.18; N, 2.52%.

The following examples illustrate pharmaceutical compositions according to the invention.

EXAMPLE 8A

Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 8B

Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 9

Parenteral injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 10

Topical formulation

|  | Amount mg |
| --- | --- |
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

I claim:

1. A compound of formula (I), or a salt or prodrug thereof:

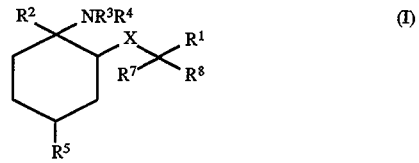

wherein

X represents O or S;

$R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$;

$R^2$ represents phenyl optionally substituted by $C_{1-6}$alkyl, $C_{1-6}$alkoxy, halo or trifluoromethyl;

$R^3$ and $R^4$ each independently represent H, $COR^a$, $CO_2R^a$ or $C_{1-6}$alkyl optionally substituted by a group selected from ($CO_2R^a$, $CONR^aR^b$, hydroxy, cyano, $COR^a$, $NR^aR^b$, and phenyl optionally substituted by $C_{1-6}$alkyl, $C_{1-6}$alkoxy, halo or trifluoromethyl);

$R^5$ represents H or $XCH_2R^6$ wherein $R^6$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ or —$CONR^aR^b$ and X is as previously defined;

$R^7$ and $R^8$ each independently represent H or $C_{1-6}$alkyl; and $R^a$ and $R^b$ each independently represent H, $C_{1-6}$alkyl, phenyl or trifluoromethyl with the exception of 2-amino-2-phenyl-1-benzyloxycyclohexane.

2. A compound as claimed in claim 1 wherein $R^7$ and $R^8$ each represent H.

3. A compound as claimed in claim 1 wherein X represents O.

4. A compound as claimed in claim 1 wherein $R^1$ represents phenyl substituted by one or more methyl or trifluoromethyl groups.

5. A compound as claimed in claim 1 wherein $R^2$ represents unsubstituted phenyl.

6. A compound as claimed in claim 1 wherein one of $R^3$ and $R^4$ represents H and the other of $R^3$ and $R^4$ represents H or $CH_2CONH_2$.

7. A compound as claimed in claim 1 wherein $R^5$ is H.

8. A pharmaceutical composition comprising a compound as claimed in claim 1 in association with a pharmaceutically acceptable carrier.

9. A process for the preparation of a compound as claimed in claim 1 which process comprises reacting a compound of formula (II):

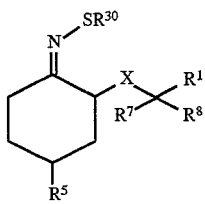

wherein $R^1$, $R^5$, $R^7$, $R^8$ and X are as defined for formula (I) and $R^{30}$ represents an alkyl or a phenyl group, with a reagent of formula $R^2$—M, where $R^2$ is as defined for formula (I) and M represents an alkali metal.

10. A method for the treatment of a physiological disorder associated with an excess of tachykinins, which method comprises administration to a patient in need thereof of a tachykinin-reducing amount of a compound according to claim 1.

11. A method according to claim 10 for the treatment of pain or inflammation.

12. A method according to claim 10 for the treatment of migraine.

13. A method according to claim 10 for the treatment of arthritis.

14. A compound which is selected from:

1-(3,5-dimethylbenzyloxy)-2-amino-2-phenylcyclohexane;

1-(3,5-dimethylbenzyloxy)-2-dimethylamino-2-phenylcyclohexane;

1-(3,5-dimethylbenzyloxy)-2-methoxycarbonylmethylamino-2-phenylcyclohexane;

1-(3,5-dimethylbenzyloxy)-2-(carboxamido)methylamino-2-phenylcyclohexane;

1-(bis-3,5-trifluoromethylbenzyloxy)-2-amino-2-phenylcyclohexane;

1-(bis-3,5-trifluoromethylbenzyloxy)-2-(carboxamido)methylamino-2-phenylcyclohexane;

1,5-bis-(3,5-dimethylbenzyloxy)-2-amino-2-phenylcyclohexane;

and salts and prodrugs thereof.

* * * * *